Figure 1:
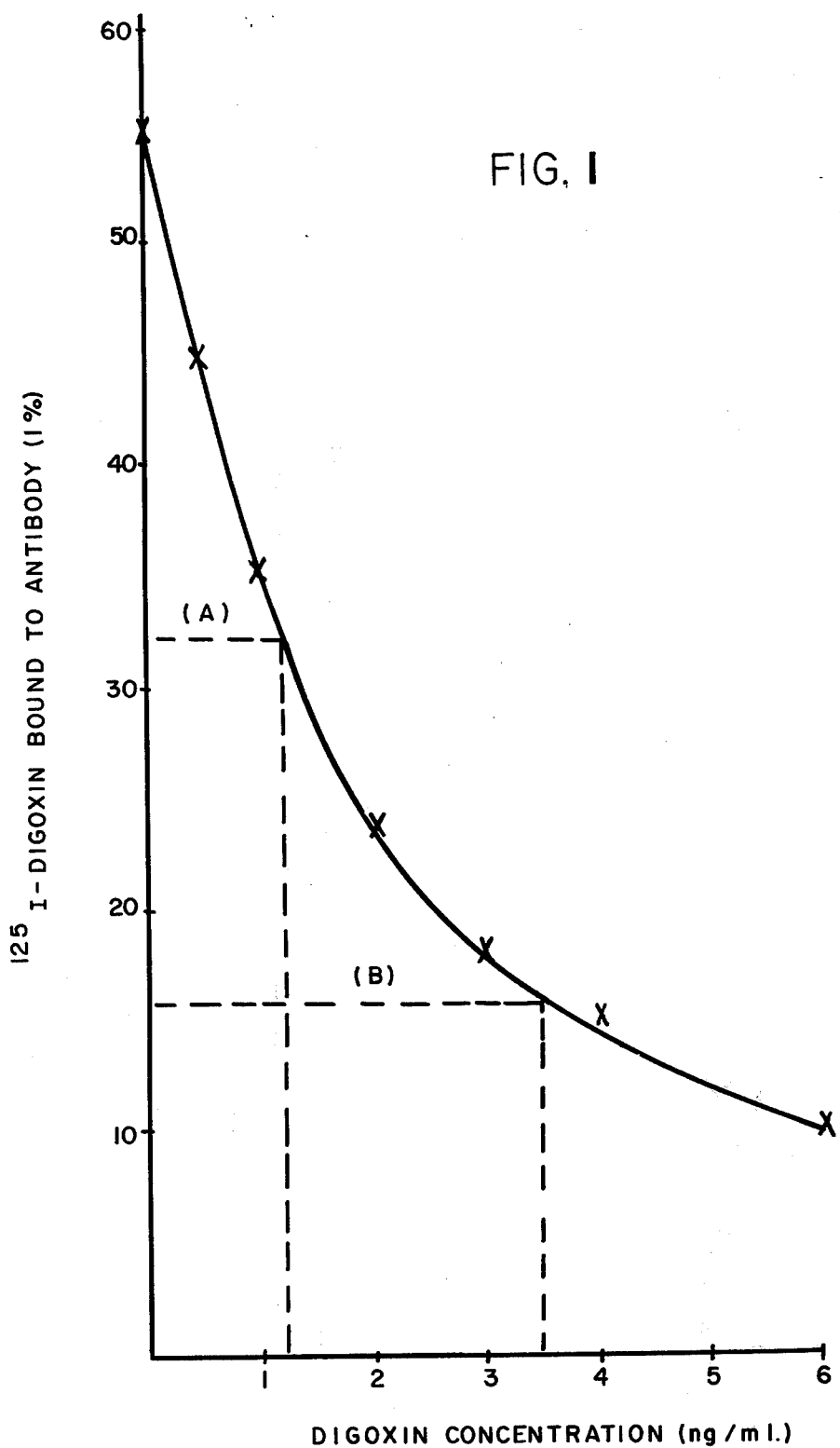

United States Patent [19]

Wilkinson

[11] 4,184,037
[45] Jan. 15, 1980

[54] DIGOXIN OXIDIZED PRODUCT

[75] Inventor: Samuel Wilkinson, Beckenham, England

[73] Assignee: Burroughs Wellcome Co., Research Triangle Park, N.C.

[21] Appl. No.: 868,896

[22] Filed: Jan. 12, 1978

Related U.S. Application Data

[63] Continuation-in-part of Ser. No. 761,781, Jan. 24, 1977, abandoned, which is a continuation of Ser. No. 662,247, Feb. 27, 1976, abandoned, which is a continuation-in-part of Ser. No. 372,072, Jun. 21, 1973, abandoned.

[30] Foreign Application Priority Data

Jun. 21, 1973 [GB] United Kingdom ............... 29279/73
Jun. 21, 1973 [GB] United Kingdom ............... 55349/73

[51] Int. Cl.$^2$ .............................................. C07J 19/00
[52] U.S. Cl. ..................................... 536/7; 23/230 R; 536/5
[58] Field of Search ......................................... 536/5, 7

[56] References Cited

U.S. PATENT DOCUMENTS 3,925,355  12/1975  Piasio et al. ............................... 536/7
3,997,525  12/1976  Guy ........................................... 536/7

FOREIGN PATENT DOCUMENTS 801275  6/1973  Belgium ...................................... 536/7

OTHER PUBLICATIONS

Butler, Jr. et al., "Proc. Nat. Acad. Sci.," vol. 57, 1967 pp. 71–78.
Oliver, Jr. et al., "The Jour. of Clinical Investigation," vol. 47, 1968, pp. 1035–1042.
Smith, "The Jour. of Pharma. and Experimental Thera." vol. 175, No. 2, 1970, pp. 352–360.

*Primary Examiner*—Johnnie R. Brown
*Attorney, Agent, or Firm*—Donald Brown

[57] ABSTRACT

Reagent of value in the radioimmunoassay of digoxin. Also provided by the invention are a radioimmunoassay method utilizing such reagent and a test kit suitable for use in performing the assay.

2 Claims, 2 Drawing Figures

DIGOXIN OXIDIZED PRODUCT

This is a continuation-in-part of application Ser. No. 761,781 filed on Jan. 24, 1977, which was a continuation of copending Ser. No. 662,247, filed Feb. 27, 1976, which was a continuation-in-part of copending Ser. No. 372,072, filed June 21, 1973, all now abandoned.

This invention relates to a reagent for the assay of a cardiac glycoside in solutions containing it, to the preparation of such reagent, to a method of performing such assays utilizing such reagent, to a test kit suitable for performing such assays, and to a method for making such a test kit.

The present invention relates more particularly to a novel reagent for the radioimmunoassay of digoxin. By use of the reagent digoxin may be assayed both in aqueous solution and in solution in mammalian (for example, human) body fluids such as plasma, serum and urine.

It is known in the art that the technique of radioimmunoassay may be adapted to the assay of digoxin. In this adapted technique a limiting, fixed quantity of antidigoxin serum, prepared by standard immunological procedures, is allowed to react with test plasma (or serum or urine) or a standard digoxin solution together with a constant amount of digoxin radioactively labelled in such a manner that the antigenic properties of the molecule are substantially unaffected. Following incubation of the mixture, free digoxin is separated from that bound to anti-body by any of the available procedures and the radioactivity of one or other of the two fractions is measured in a radio-activity counter. The binding of labelled digoxin is progressively inhibited by increasing amounts of unlabelled digoxin due to competition between the two species for the specific binding sites on the antibody. The concentration of digoxin in the plasma under test may readily be determined by reference to a standard curve prepared at the same time.

Hitherto, those assay methods described in the literature have involved the use of tritiated digoxin as the labelled compound with the associated disadvantages of low specific radioactivity and the need for measuring samples in a liquid scintillation counter.

It has now been found that a novel antigenically satisfactory reagent, having high specific radioactivity and permitting measurement of samples with the more convenient solid crystal scintillation counter, and stable when freeze-dried, may be prepared by the sequential steps of:

(a) selective oxidation at the 15'- and 16'-positions of the terminal digitoxose residue of digoxin;
(b) reacting the product of step (a) with tyrosine methyl ester, to yield the digoxin-tyrosine methyl ester conjugate;
(c) selectively reducing the product conjugate of step (b), to yield the reduced conjugate; and
(d) radioiodinating the product reduced conjugate of step (c) with $^{125}I$.

Selective oxidation of the terminal digitoxose residue (step (a)) may be effected by any agent conventionally used for the scission of 1:2-glycols, but lead tetraacetate and periodic acid and its soluble salts are preferred. The selective reduction (step (c)) of the product conjugate of step (b) may be effected by use of an agent selected from the boranes, borohydrides and aluminium hydrides known in the art, for example potassium borohydride, sodium borohydride, lithium borohydride and lithium aluminium hydride. Radioiodination (step (d)) may be performed by any of the known procedures but is preferably carried out using a modification of the chloramine T procedure standard in the art.

It will be appreciated that in principle any of the radioisotopes of iodine ($^{123}I$, $^{124}I$, $^{125}I$, $^{126}I$, $^{128}I$, $^{129}I$, $^{130}I$, $^{131}I$ and $^{132}I$) may be introduced into the product reduced conjugate of step (c) but that, from considerations of availability, half-life and specific activity, $^{125}I$ and $^{131}I$ are preferred and $^{125}I$ most preferred.

The assay of digoxin may be conveniently effected by use of a test kit comprising at least four vessels,
a first vessel containing a buffer solution,
a second vessel containing a mixture of (a) an antiserum raised in a species of mammal or bird reactive against digoxin and (b) an antiserum raised in a second species of mammal or bird reactive against the immunoglobulins of the first species,
a third vessel containing a solution of the radioiodinated reagent as hereinabove described; and
a fourth vessel containing a standard solution of digoxin in serum from a species of mammal or bird other than the species in which the antiserum reactive against digoxin was raised.

Optionally the contents of one or more of the vessels are in the freeze dried state, and conveniently the kit comprises in addition to the first, second and third vessels identified above a plurality of vessels each containing a standard solution of digoxin in serum from a species of mammal or bird other than the species in which the antiserum reactive against digoxin was raised, the standard solutions being of different concentrations the one from the other.

In various aspects therefore there are provided by the present invention:
the product reduced conjugate of step (c) and the radioiodinated reagent derived therefrom as hereinabove described, and methods for their preparation as herein described;
a method for the radioimmunoassay of digoxin comprising in sequence the steps of (a) reacting together a mixture of digoxin, an antiserum to digoxin and the radioiodinated reagent as hereinabove described, (b) separating the antibody-bound reagent fraction from the non-antibody-bound fraction, and (c) measuring the radioactivity of one of the said fractions;
a test kit, as herein described, suitable for use in the radioimmunoassay of digoxin; and
a method of making a test kit, as herein described, suitable for use in the radioimmunoassay of digoxin comprising the assembling in kit form of the vessels as described.

The following Examples serve to describe the present invention, by way of illustration only, and do not in any way limit the invention described above. All temperatures are in degrees Celsius. Example 1 relates to the preparation, in the manner described above, of the digoxin-tyrosine methyl ester conjugate identified above and the selective reduction of this to the reduced conjugate; the structure of this latter was confirmed by nuclear magnetic resonance spectroscopy. Example 2 relates to the radioiodination of the reduced conjugate to yield the reagent identified above. In Examples 3 and 4 the reagent identified as "radioactive digoxin" was the product of the process of Example 2.

In Example 2 the reagent identified as "chloramine T" has the systematic name (N-chloro-p-toluenesulphonamido) sodium.

EXAMPLE 1

Preparation of (a) the digoxin-tyrosine methyl ester conjugate and (b) the reduced conjugate Digoxin (2.5 g.) was dissolved in a mixture of methanol (150 ml.) and chloroform (50 ml.) A solution of sodium periodate (25 ml., 10% w/v) was added with stirring over a period of 30 minutes. After an additional 90 minutes the mixture was filtered, water (25 ml.) added to the filtrate and the solvents removed in vacuo. The residue was extracted with chloroform (5×100 ml.), the solution washed with water (50 ml.) dried (magnesium sulphate) and concentrated in vacuo.

The residue was dissolved in ethanol (30 ml.), L-tyrosine methyl ester hydrochloride (2.225 g.) and triethylamine (1.34 ml.) added and the mixture stirred for one hour. Ethanol (30 ml.) was added and with stirring sodium borohydride (5.14 g.) introduced portionwise over ten minutes. Stirring was continued for two hours, then glacial acetic acid added until there was no further evolution of hydrogen. After addition of water (50 ml.) the ethanol was removed in vacuo and the residue extracted with chloroform (3×100 ml.). The extract was washed successively with 50 ml. portions of water, 0.5N-hydrochloric acid and water, dried (magnesium sulphate) and concentrated in vacuo to give an amorphous solid.

The above product was purified by chromatography on neutral alumina with the solvent mixture methanol: chloroform (1:9 v/v) monitoring the eluates by means of an ultraviolet absorptiometer. The fractions absorbing at 254 mμ were combined and the solvent was removed in vacuo. The amorphous residue was homogeneous by thin layer chromatography (alumina plates; solvent methanol: chloroform (2:8 v/v), $R_f$ 0.60) and gave positive reactions with Pauly's reagent (tyrosine) and Raymond's reagent (cardenolides). Analysis by nuclear magnetic resonance spectroscopy indicated that the ratio of phenol to cardenolide was 1:1.

Characterizing data for the reduced conjugate are as follows:

(a) Infrared spectroscopy

Figure 2:
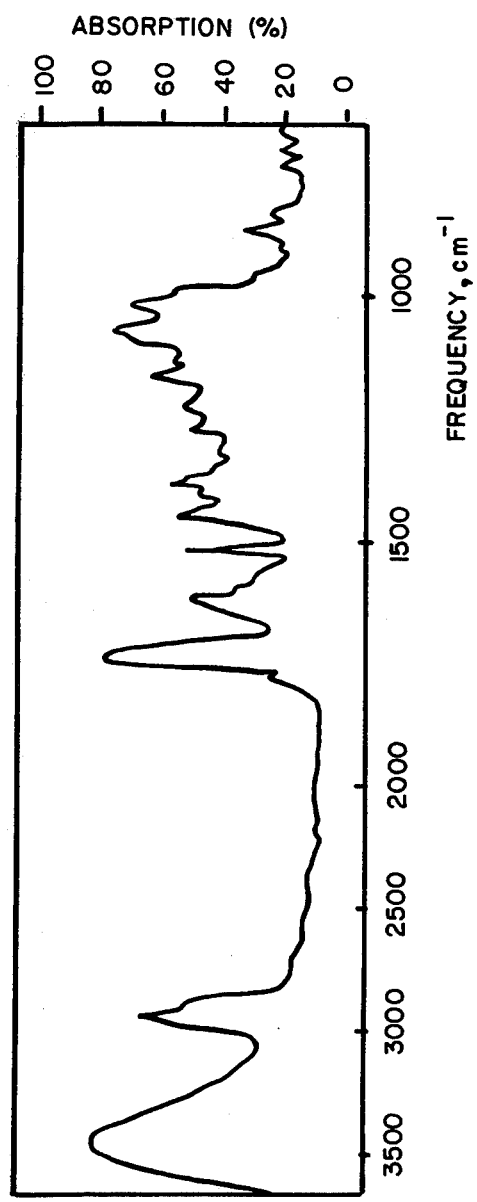

The infrared absorption spectrum of the compound (1.48 mg.) in a potassium bromide disc (16 mm. diameter) is shown in the accompanying FIG. 2. The principle bands are:

| cm$^{-1}$ | |
|---|---|
| 863 | phenyl |
| 1017 | |
| 1066 | —C— OH and C—O—C largely from carbohydrate phenolic C—OH |
| 1167 | |
| 1380 | |
| 1446 | |
| 1513 | phenyl |
| 1612 | phenyl |
| 1732 | lactone |
| 1776 | |
| 2930 | |
| 3425 | |

(b) Nuclear magnetic resonance spectroscopy

The N.M.R. spectrum was recorded at 100 MHz in deuterochloroform containing hexadeutero-dimethyl-sulphoxide to obtain a clear solution. Chemical shifts, coupling and integration were in agreement with the gross structure. Integral measurements of the aromatic protons to the "olefinic" proton showed that with respect to the genin there were 1.006 tyrosine residues.

| Protons | Observed Chemical Shifts (ppm) | Characteristics |
|---|---|---|
| Phenolic | 6.95 | doublet |
| Phenolic | 6.75 | doublet |
| Lactone | 5.95 | singlet |
| Angular CH$_3$ | 0.80 and 0.92 | singlets |

EXAMPLE 2

Iodination of the digoxin—tyrosine methyl ester reduced conjugate of Example 1

To sodium iodide ($^{125}$I, 2 mc) in sodium phosphate buffer (0.5 M, 25 μl., pH 7.5) was added the reduced conjugate (2.5 μg.) in 10% aqueous ethanol (12.5 μl.), and chloramine T (10 μg.) in the same phosphate buffer (20 μl.). After stirring the mixture for 30 seconds, using a miniature magnetic stirrer, the reaction was stopped by the addition of sodium metabisulphite (100 μg.) in phosphate buffer as before (20 μl.). Dimethylformamide (0.5 ml.) and deionised water (0.3 ml.) were then added and the mixture transferred to a column (25×15 mm.) of Amberlite IRA 400 (Cl form) prewashed with deionised water. The column was eluted with TRIS [tris (hydroxymethyl) aminomethane]-hydrochloric acid buffer (composition as below) (pH 8.5): 1 ml. fractions were collected, the bulk of the iodinated derivative appearing in the third to sixth portions.

Typical results show a 70–85% incorporation of the iodine into the conjugate.

The buffer used to elute the column had the following composition:

| TRIS | to 0.1M |
|---|---|
| Sodium chloride | to 1.0M |
| Tween 20 | to 0.5% w/w |
| Sodium azide | to 0.5% w/w |

Concentrated hydrochloric acid to pH 8.5

EXAMPLE 3

Digoxin Radioimmunoassay

The assay was carried out in polystyrene test tubes (8×63mm using the following reagents:

1. Diluent buffer. Phosphate-saline buffer (pH 7.4) having the composition detailed below was used for diluting all reagents and samples
1 liter of the buffer contained:

| Sodium dihydrogen phosphate dihydrate: | 6.24g |
|---|---|
| Disodium ethylenediamine tetraacetic acid: | 3.72g. |
| Bovine serum albumin: | 5.0g. |
| Sodium azide: | 1.0g. |
| Sodium chloride: | 9.0g. |

After making up to 900 ml. with deionised water the pH was adjusted to 7.4 with 5N - sodium hydroxide and water added to 1 liter.

2. Anti-digoxin serum (rabbit) at a dilution which bound approximately 50 percent of the radioactive digoxin added, in the absence of unlabelled digoxin.

3. Radioactive digoxin: digoxin-tyrosine methyl ester labelled with $^{125}I$, working strength solution 2 ng./ml.
4. Standard digoxin Stock solution in phosphate-saline buffer as above of 100 ng./ml. diluted 1:12.5 to give first working strength dilution of 8 ng./ml., then doubling dilutions to give 4.0, 2.0, 1.0, 0.5 and 0.25 ng./ml.
5. Normal horse serum
6. Normal rabbit serum, diluted 1:500
7. Precipitating serum antiserum to rabbit gamma-globulin diluted 1:20.

Procedure

Test tubes were set up in triplicate for the blank (to which no antiserum was added), the zero standard, digoxin standards and plasma samples. 0.4 ml. Of normal rabbit serum (1:500 dilution) was added to each tube followed by 0.1 ml. volumes of standard digoxin solution, normal horse serum (to control and standard tubes only), test plasma, radioactive digoxin solution and anti-digoxin serum. 0.1 ml. Radioactive digoxin solution alone was pipetted into polystyrene tubes as a sample of the total radioactivity added. The contents of the tubes were mixed on a vortex mixer and the tubes incubated for 30 minutes at room temperature. 0.1 ml. Precipitating serum (1:20 dilution) was then added, the contents of the tubes mixed and the tubes stood overnight at 4° C. After centrifugation for 20 minutes at 2,000 g, aspiration of the supernatant and addition of 1 ml. wash buffer (composition identical with that of the diluent buffer) was followed by further centrifugation and aspiration. The radioactivity in the antibody-bound fraction was measured in a well-type scintillation counter.

The concentration of digoxin in the plasma under test was determined by reference to a curve prepared from the results obtained with the standard digoxin solutions.

EXAMPLE 4

Digoxin Radioimmunoassay

A further assay was carried out in glass test tubes using the following reagents:
1. Wash Buffer: phosphate-saline buffer (pH 7.4) prepared as follows:

| | |
|---|---|
| Sodium chloride | 9.0g. |
| Sodium dihydrogen phosphate, dihydrate | 6.2g |
| Bovine albumin powder | 5.0g. |
| Sodium azide | 1.0g. |
| Deionised water | to 900 ml. |
| pH adjusted to 7.4 with sodium hydroxide | |
| Deionised water | to 1 liter |

2. Digoxin Binding Reagent: a mixture of
(a) rabbit anti-digoxin serum, and (b) donkey antiserum to rabbit gamma-globulin, the reagent reconstituted as required from freeze dried material by addition of deionized water.
3. Radioactive Digoxin: digoxin-tyrosine methyl ester labelled with $^{125}I$, working strength solution of 2 ng./ml. in buffer as in I. above, reconstituted as required from freeze dried material by addition of deionized water.
4. Standard Digoxin: solutions in bovine serum at concentrations of zero, 0.5, 1.0, 2.0, 3.0, 4.0 and 6.0 ng./ml., reconstituted as required from freeze dried material by addition of deionized water.

Procedure

Test tubes were set up in duplicate with the composition as indicated below, the reagents being added in the order shown:

| | Zero and other standards | Test plasma |
|---|---|---|
| Standard digoxin solution (ml.): | 0.1 | — |
| Test plasma (ml.): | — | 0.1 |
| Radioactive digoxin solution (ml.): | 0.1 | 0.1 |
| Digoxin binding reagent (ml.): | 0.1 | 0.1 |

In addition, 0.1 ml. of radioactive digoxin solution alone was pipetted into duplicate tubes as a sample of the total radioactivity added.

After addition of the last reagent the contents of each tube were mixed using a vortex mixer and the tubes stood at room temperature for 1½ hours. At the end of this period wash buffer (1 ml.) was added to each tube (excluding those containing radioactive digoxin solution alone) and the tubes and contents centrifuged at 2000 g for 20 minutes. The supernatant was then discarded and the radioactivity of the precipitate (the antibody-bound fraction) measured using a well-type crystal scintillation counter.

Using this technique the concentration of digoxin in two test samples of plasma was determined by reference to a curve prepared from the results obtained with the standard digoxin solutions, as shown in the accompanying FIG. 1. The concentration of digoxin in sample (A) was determined as 1.2 ng./ml. and that in sample (B) as 3.5 ng./ml.

What I claim is:
1. The material obtainable by:
(a) selectively oxidising digoxin at the 15'- and 16'-positions of the terminal digitoxose residue thereof using sodium periodate;
(b) reacting the product of step (a) with tyrosine methyl ester; and
(c) selectively reducing with sodium borohydride the product of step (b); which material
(i) absorbs at a wavelength of 254 mµ when in solution in the mixture methanol:chloroform, 1:9 (v/v);
(ii) is homogeneous by thin layer chromatography using alumina plates and the solvent system methanol:chloroform, 2:8 (v/v) and has Rf 0.60 in this system;
(iii) gives positive reactions with Pauly's reagent (for tyrosine) and Raymond's reagent (for cardenolides) and has a phenol to cardenolide ratio of 1:1;
(iv) has an infrared absorption spectrum substantially as shown in FIG. 2; and
(v) whereof the nuclear magnetic resonance spectrum recorded at 100 MHz in deuterochloroform/hexadeuterodimethylsulphoxide has the following features:

| Protons | Observed chemical shifts (ppm) | Characteristics |
|---|---|---|
| Phenolic | 6.95 | doublet |
| Phenolic | 6.75 | doublet |
| Lactone | 5.95 | singlet |
| Angular $CH_3$ | 0.80 and 0.92 | singlets | where ppm (parts per million) is with reference to tetramethylsilane internal standard.
2. The material obtainable by radio-iodinating the material defined in claim 1 with $^{125}I$.

* * * * *